(12) United States Patent
Kim et al.

(10) Patent No.: US 8,957,221 B2
(45) Date of Patent: Feb. 17, 2015

(54) METHOD FOR PREPARING AMINO-TRIAZOLINONE

(75) Inventors: Keun Sik Kim, Suncheon-si (KR); Yeon Tak Choi, Suncheon-si (KR)

(73) Assignee: KS Laboratories Co., Ltd., Suncheon-si (KR)

( * ) Notice: Subject to any disclaimer, the term of this patent is extended or adjusted under 35 U.S.C. 154(b) by 0 days.

(21) Appl. No.: 14/235,753

(22) PCT Filed: Jul. 27, 2012

(86) PCT No.: PCT/KR2012/006031
§ 371 (c)(1),
(2), (4) Date: Jan. 28, 2014

(87) PCT Pub. No.: WO2013/015654
PCT Pub. Date: Jan. 31, 2013

(65) Prior Publication Data
US 2014/0163239 A1    Jun. 12, 2014

(30) Foreign Application Priority Data

Jul. 28, 2011   (KR) .................. 10-2011-0075386

(51) Int. Cl.
 C07D 249/12    (2006.01)
(52) U.S. Cl.
 CPC ................... *C07D 249/12* (2013.01)
 USPC ...................................... 548/263.8

(58) Field of Classification Search
None
See application file for complete search history.

(56) References Cited

U.S. PATENT DOCUMENTS

| | | | |
|---|---|---|---|
| 4,952,701 A | 8/1990 | Müller et al. |
| 5,153,326 A | 10/1992 | König et al. |
| 5,693,821 A | 12/1997 | Diehr et al. |
| 5,756,752 A | 5/1998 | Diehr et al. |
| 5,912,354 A | 6/1999 | Desai et al. |
| 5,977,401 A | 11/1999 | Wroblowsky |

*Primary Examiner* — Michael Barker
(74) *Attorney, Agent, or Firm* — Seed IP Law Group PLLC

(57) ABSTRACT

The present invention relates to a method for preparing an amino-triazolinone which can be used as a raw material for amicarbazone and has chemical formula (I). The method for preparing the amino-triazolinone includes the steps of: reacting an acyl hydrazide of chemical formula (II) with a carbamating agent of chemical formula (III) or (IV) so as to obtain a hydrazine carboxylic acid of chemical formula (V); and reacting the thus-obtained hydrazine carboxylic acid of chemical formula (V) with a hydrazine hydrate under the presence of a base catalyst. According to the present invention, the amino-triazolinone may be stably prepared without using safety equipment or safety facilities for a possible leakage of phosgene, which has been used as a conventional reactant. Thus, manufacturing costs for amicarbazone, which is used as a herbicide for farm products such as sugar cane, corn, or the like, can be reduced so as to achieve improved price competitiveness, and further to achieve improved cost competitiveness compared to other herbicides.

12 Claims, 2 Drawing Sheets

METHOD FOR PREPARING AMINO-TRIAZOLINONE

CROSS-REFERENCE TO RELATED APPLICATIONS

This application is a U.S. national stage application filed under 35 U.S.C. §371 of International Patent Application PCT/KR2012/006031, accorded an international filing date of Jul. 27, 2012, which claims the benefit of Korean (KR) Application No. 10-2011-0075386 filed Jul. 28, 2011.

TECHNICAL FIELD

The present invention relates to a novel method for preparing amino-triazolinone of Chemical Formula I as a key intermediate for preparing amicarbazone which is a triazolinone-based herbicidal active compound:

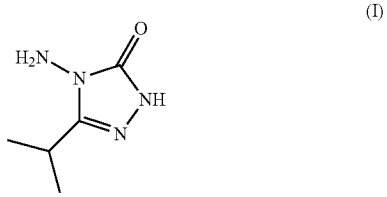

The compound is a white powder having a chemical name of 3-isopropyl-4-amino-1,2,4-triazole-5-on (or 3H-1,2,4-triazole-3-on) and a melting point of 168 to 176° C. Amino-triazolinone is a key raw material of amicarbazone used as an herbicide for field crops such as sugar cane, corn, and the like.

BACKGROUND ART

Amino-triazolinone of the present invention is synthesized by using hydrazine as a starting raw material and adding phosgene which is a poisonous gas in the middle as shown in the following Reaction Formula. The above-described process, which is the first developed process by Bayer AG in Germany, finally produces amicarbazone which is a prominent plant growth regulator. The amicarbazone is mainly used in a large farm producing sugar canes and cones, and in accordance with an increased demand for the sugar cane which is a raw material for preparing bioethanol and a raw material of raw sugar, a demand for an herbicide has also become increased.

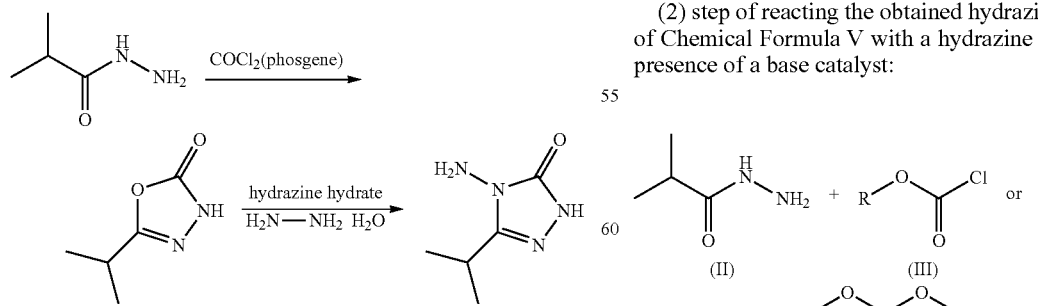

Since the amino-triazolinone of the present invention was known in a prior document (see J. Heterocyclic Chem., 21(6), 1769~74 (1984)), methods of preparing the same have been registered as a patent; however, these patents are mostly directed to a method for preparing amino-triazolinone using phosgene. Representative inventions using phosgene have been disclosed in U.S. Pat. No. 4,952,701 (filed in 1988), U.S. Pat. No. 5,693,821 (filed in 1996) and U.S. Pat. No. 5,912,354 (filed in 1998) in detail (see the known patent documents for details).

DISCLOSURE

Technical Problem

As described in the known method for preparing amino-triazolinone, a dangerous phosgene gas has been used in the preparation method. As well-known in the art, since the phosgene gas is poisonous, it has fatal health hazards at the time of leakage, and always contains riskiness when being developed. In addition, since amino-triazolinone is prepared at a high temperature of 70 to 80° C. or higher in a phosgenation reaction, the high-temperature reaction with the phosgene which is a gas at room temperature is significantly dangerous (U.S. Pat. No. 5,756,752 (filed in 1997).

Further, an increase in equipment investment due to supplementation of safety equipment or safety facilities for a possible leakage of the poisonous phosgene gas also causes an increase in the preparation cost of amino-triazolinone and amicarbazone which is the final product of the amino-triazolinone to be prepared in the present invention, thereby decreasing the price competitiveness of the final product, such that the cost competitiveness becomes decreased as compared with other herbicides.

Therefore, a process capable of stably preparing amino-triazolinone which is an essential raw material of amicarbazone which is a herbicide as a plant growth regulator is required to be developed, and a novel process capable of decreasing the preparation cost of the amino-triazolinone is also required to be developed.

Technical Solution

According to an exemplary embodiment of the present invention, there is provided a method for preparing amino-triazolinone of Chemical Formula I, the method including:

(1) step of reacting an acyl hydrazide of Chemical Formula II with a carbamating agent of Chemical Formula III or IV to obtain a hydrazinecarboxylic acid of Chemical Formula V; and (2) step of reacting the obtained hydrazinecarboxylic acid of Chemical Formula V with a hydrazine hydrate under the presence of a base catalyst:

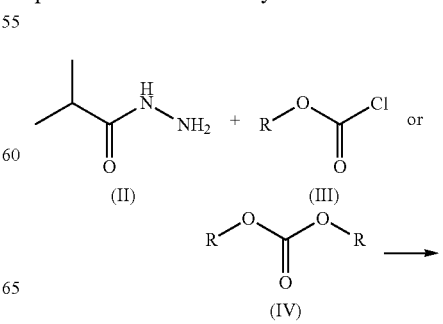

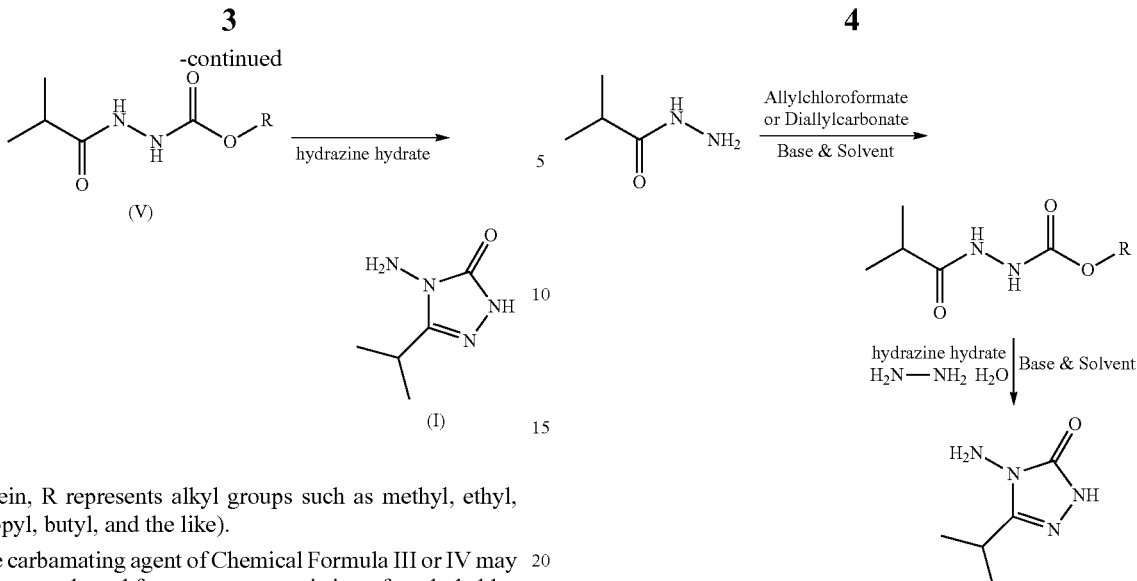

(wherein, R represents alkyl groups such as methyl, ethyl, isopropyl, butyl, and the like).

The carbamating agent of Chemical Formula III or IV may be any one selected from a group consisting of methyl chloroformate, ethyl chloroformate, isopropyl chloroformate, dimethyl carbonate, diethyl carbonate.

The base may be any one selected from a group consisting of NaOH, KOH, NaHCO₃, Na₂CO₃, KHCO₃, K₂CO₃, CaCO₃.

The carbamating agent of Chemical Formula III used in step (1) above may be methyl chloroformate (MCF), and a solvent used in step (1) above may be selected from methylene chloride (MC), water, methanol and toluene and a reaction temperature used in step (1) above may be 10 to 25° C.

The base used in step (2) above may be NaOH or KOH, and a solvent used in step (2) above may be toluene and a reaction temperature used in step (2) above may be 90 to 100° C.

Advantageous Effects

According to the present invention, amino-triazolinone may be stably prepared without using safety equipment or safety facilities for a possible leakage of phosgene which has been used as a conventional reactant. Therefore, the preparation cost of amicarbazone which is the final product may be decreased to increase price competitiveness and to increase cost competitiveness as compared to other herbicides.

BEST MODE

Figure 1:
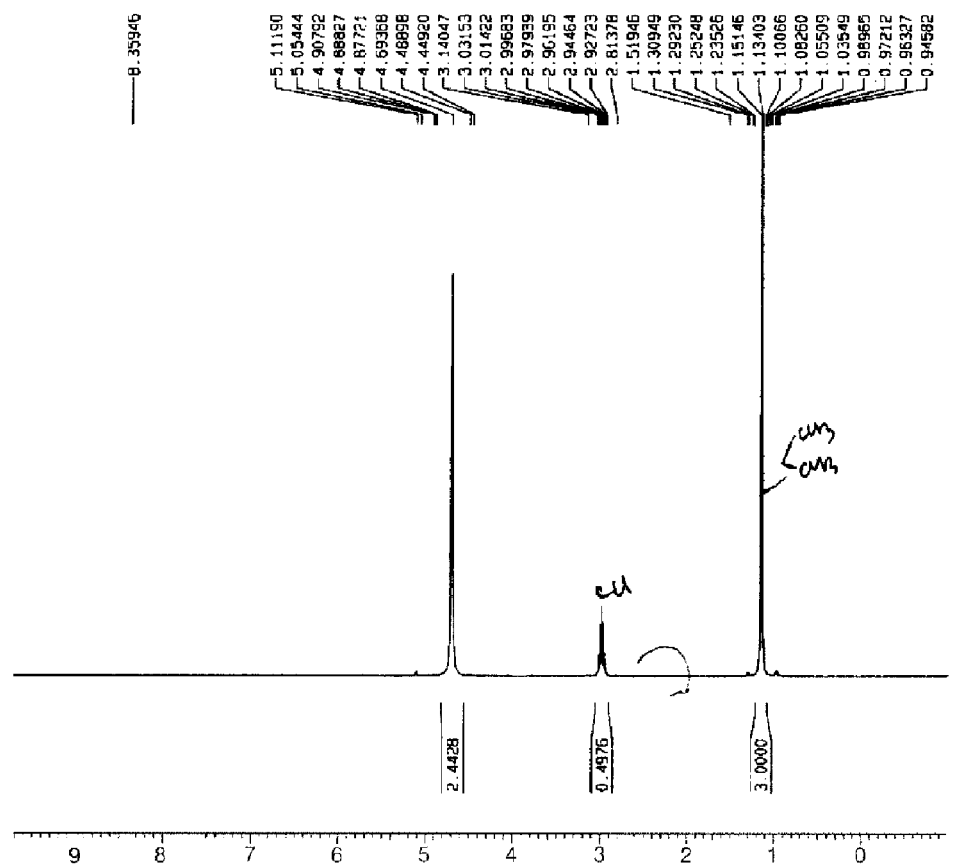
FIG. 1 shows H-NMR data (D₂O, 400 MHz) of the final product obtained by Example 7.

As shown in the following Reaction Formula, the present invention will be performed by two steps, (1) step of reacting an acyl hydrazide of Chemical Formula II with a carbamating agent of Chemical Formula III or IV to obtain a hydrazinecarboxylic acid of Chemical Formula V, and (2) step of reacting the obtained hydrazinecarboxylic acid of Chemical Formula V with a hydrazine hydrate:

(wherein, R represents alkyl groups such as methyl, ethyl, isopropyl, butyl, and the like).

Isobutyric acid hydrazide which is a starting material in step (1) of the present invention is a known compound of Chemical Formula II:

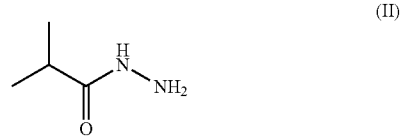

(II)

In the present invention, isobutyric acid hydrazide was synthesized with reference to Example 1 described in U.S. Pat. No. 5,756,752 (filed in 1997), wherein the specific synthesis process thereof will be omitted in the present invention.

In addition, a carbamating agent (—N—CO—O—) used as a starting material in step (1) of the present invention indicates a compound capable of synthesizing carbamate using alkylchloroformate (R—O—CO—Cl) or dialkylcarbonate. The carbamating agent in the present invention is preferably alkylchloroformate or dialkylcarbonate, and in particular, among them, a methyl group is the most preferred and other groups are possible to be used. Alkylchloroformate and dialkylcarbonate used in the present invention have the following Chemical Formulas III and IV, respectively:

(III)

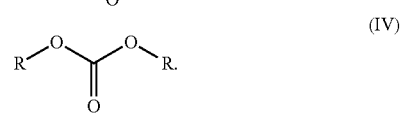

(IV)

In addition, it is preferred that a functional group 'R' in the dialkylcarbonate is a methyl group, and is of Chemical Formula:

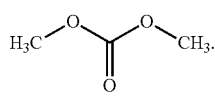

In addition, the hydrazinecarboxylic acid (referred to as '2-(2-methyl-1-oxopropyl)-methyl ester') used in step (2) of the present invention is of Chemical Formula V, and the hydrazinecarboxylic acid obtained by step (1) will directly used in step (2):

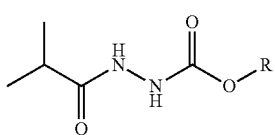

(V)

(wherein, R represents alkyl groups such as methyl, ethyl, isopropyl, butyl, and the like).

Lastly, hydrazine hydride used in step (2) above of the present invention is generally mixed with a base compound (which is capable of being dissolved into water to be used) and a polar organic solvent at room temperature and the obtained mixture is heated up to a desired reaction temperature. Then, the hydrazinecarboxylic acid obtained as an intermediate represented by the Chemical Formula (V) will be slowly introduced into the heated reaction mixture, and the reaction mixture will be maintained within a designated temperature range while being stirred if needed, until the reaction is ultimately completed.

The reaction according to the present invention is performed under the presence of a base compound (which is capable of being dissolved into water). The base compound appropriate for the present application is an inorganic or organic base or an acid acceptor which is available on the market. An example of the base compound includes alkali metal or alkaline earth metal acetates, amides, carbonates, hydrocarbon salts, hydrides, hydroxides, alkoxides, for example, sodium acetate, potassium acetate or calcium acetate, sodium carbonate, potassium carbonate, calcium carbonate, sodium hydrogen carbonate, potassium hydrogen carbonate, calcium hydrogen carbonate, lithium hydride, sodium hydride, calcium hydride, lithium hydroxide, sodium hydroxide, potassium hydroxide, calcium hydroxide, or sodium or calcium methoxide, ethoxide, or n- or i-propoxide, or n-, i-, s- or t-butoxide, and the like. As the base compound in performing the reaction according to the present invention, alkali metal hydroxides such as lithium hydroxide, sodium hydroxide and potassium hydroxide are preferably used. In particular, sodium hydroxide is more preferably used because of capable of being dissolved into water.

The reaction according to the present invention is performed under the presence of a polar organic solvent. An example of the polar organic solvent includes sulfoxides such as dimethyl sulfoxide as well as dialkyl ethers (for example, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or diethyl ether, diethylene glycol dimethyl ether or diethyl ether); dialkyl ketones (for example, methyl ethyl ketone, methyl i-propyl ketone or methyl i-butyl ketone, nitriles (for example, acetonitrile, propionitrile, butyronitrile or benzonitrile); amides (for example, N,N-dimethyl-formamid (DMF), N,N-dimethyl-acetamide, N-methyl-formanilide, N-methyl-pyrrolidone or hexamethyl-phosphoramide); esters (for example, methyl, ethyl, n- or i-propyl, n-, i- or s-butyl acetate); alcohols (for example, ethanol, n- or i-propanol, n-, i-, s- or t-butanol). As the alcohol used as a solvent in performing the reaction according to the present invention, methanol, ethanol, n- or i-propanol, n-, i-, s- or t-butanol are preferably used.

The reaction step according to the present invention may be divided into step (1) using a carbamating agent and step (2) which is a cyclization reaction; however, step (2) which is the cyclization reaction may be performed without separation and purification of the intermediate.

In performing the reaction according to the present invention, a reaction temperature may be changed within a relatively wide range. In general, the reaction temperature in step (1) using a carbamating agent is 0 to 60° C., and in the reaction using alkylchloroformate, the reaction temperature is preferably 0 to 30° C., more preferably, 10 to 25° C. In addition, in the reaction using alkylcarbonate, the reaction temperature is 50 to 70° C., and preferably, 55 to 65° C. In step (2) using hydrazine hydride, the reaction temperature is 50 to 150° C., preferably, 70 to 130° C., more preferably, 90 to 110° C.

The reaction according to the present invention is generally performed under a normal pressure. However, the reaction according to the present invention may be performed under an increased pressure or a decreased pressure, for example, 0.1 to 10 bars. In the case of using a low-boiling alcohol, the reaction is preferably performed under an increased pressure.

With respect to a ratio of a reactant in step (1) used in the present invention, the carbamating agent (III) or (IV) is used in an equivalent of 0.9 to 1.5 based on carbohydrazide (II). In the case of using the carbamating agent in an equivalent less than 0.9, a yield may not be sufficient, and in the case of using carbamating agent in an equivalent more than 1.5, an impurities content may be increased or purification thereof may be difficult, which is not economically preferred. The most preferred range of the used carbamating agent is an equivalent of 0.98 to 1.05. In addition, with respect to a range of the used base, in the case of using chloroformate (III) and an alkali metal, an equivalent of 1.0 to 1.5 may be used based on the carbamating agent. In the case of using an equivalent less than 1.0, impurities content may be increased or a yield thereof may be decreased, and in the case of using an equivalent more than 1.50, a yield and purity thereof may be deteriorated. In addition, in the case of using dialkyl carbonate (IV), the reaction of the present invention may be performed even in a catalytic content, that is, an equivalent of 0.1 to 1.0. In the case of using an equivalent less than 0.1, the reaction rate may be significantly slow which may deteriorate a yield thereof, and in the case of using an equivalent more than 1, a side-reaction may occur, which is not economically preferred. In the cyclization reaction which is step (2), an equivalent of the hydrazine hydride based on the intermediate represented by Chemical Formula V may be 0.98 to 1.2. In the case of using the hydrazine hydride in an equivalent of 1 or less, a yield thereof may be deteriorated, and in the case of using the hydrazine hydride in an equivalent of 1.2 or more, impurities may be produced, which is not economically preferred. In addition, the base may be used in an equivalent of 0.01 to 1.0, preferably, an equivalent of 0.05 to 0.2 as a catalytic content. In the case of using an equivalent less than 0.05, the reaction rate may be slow and a yield thereof may be deteriorated, and in the case of using an equivalent of 1 or more, impurities may be produced, which is not economically preferred.

Hereinafter, the present invention will be described by representative examples in detail, but is not limited thereto.

First, the following Examples 1 to 6 show a process of preparing a hydrazinecarboxylic acid which is an intermediate using various carbamating agents and bases in the preparation method according to the present invention, the following Examples 7 and 8 show a process of preparing amino-triazolinone using the intermediate obtained by Examples 1 to 6:

Example 1

Preparation of Intermediate Using Methylchloroformate (MCF)/NaOH/MC

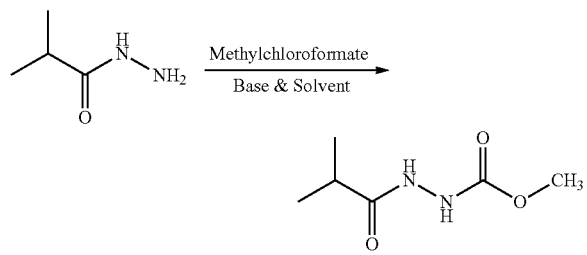

204 g (2.0 mole) of Iso-butyric acid hydrazide, methylene chloride (MC) 600 ml and 170 g (2.1 mole) of 50% of NaOH aqueous solution were mixed in a four-neck flask reactor equipped with a Dean-Stark trap. The obtained mixture was cooled at a temperature of 10° C. or less and 190 g (1.0 equivalent) of methylchloroformate (MCF) was slowly added thereto for 3 to 5 hours while controlling temperature with strong stirring. When the addition was completed, a reaction temperature was maintained by controlling it from 10° C. up to room temperature and the reaction was complete. After the reaction was completed, the stirring was stopped, followed by layer-separation, thereby separating an organic layer (MC) positioned in a lower portion of the flask reactor, and the separated organic layer was washed twice with water 600 ml. Then, the obtained organic layer was concentrated to obtain a hydrazine carboxylic acid 314 g (yield 98%) having a purity of 99 area % by GC as an intermediate, which was possible to be directly used in a next reaction without additional purification.

Example 2

Preparation of Intermediate Using Methylchloroformate (MCF)/NaOH/Methanol

Iso-butyric acid hydrazide 204 g (2.0 mole), methanol 500 ml and 50% NaOH aqueous solution 176 g (1.1 moles) were mixed in a four-neck flask reactor equipped with a Dean-Stark trap. The obtained mixture was cooled at a temperature of 10° C. or less and methylchloroformate(MCF) 206 g (1.1 equivalents) was slowly added thereto for 3 to 5 hours while controlling temperature with strong stirring. When the adding was completed, a reaction temperature was maintained by controlling it from 10° C. up to room temperature and the reaction was complete. After the reaction was completed, the reactant was crystallized while methanol was vacuum-evaporated. After the obtained solid was filtered, the obtained cake was washed with water twice and dried. The obtained solid was a hydrazine carboxylic acid 292 g (yield 91%) having a purity of 98.9 area % by GC as a white solid and an intermediate, which was possible to be directly used in a next reaction without additional purification.

Example 3

Preparation of Intermediate Using Methylchloroformate (MCF)/KOH/Methanol

Iso-butyric acid hydrazide 102 g (1.0 mole), methanol 300 ml and 40% KOH aqueous solution 145 g (1.05 equivalents) were mixed in a four-neck flask reactor equipped with a Dean-Stark trap. The obtained mixture was cooled at a temperature of 10° C. or less and 95 g (1.0 equivalent) of methylchloroformate (MCF) was slowly added thereto for 2 to 3 hours while controlling temperature with strong stirring. When the adding was completed, a reaction temperature was maintained by controlling it from 10° C. up to room temperature and the reaction was completed. After the reaction was completed, the reactant was crystallized while methanol was vacuum-evaporated. After the obtained solid was filtered, the obtained cake was washed with water twice and dried. The obtained solid was a hydrazine carboxylic acid 142 g (yield 88%) having a purity of 98.5 area % by GC as a white solid and an intermediate, which was possible to be directly used in a next reaction without additional purification.

Example 4

Preparation of Intermediate Using Methylchloroformate(MCF)/N,N-triethylamine(TEA)

Iso-butyric acid hydrazide 102 g (1.0 mole), methanol 300 ml and N,N-triethylamine (TEA) 106 g (1.05 equivalents) were mixed in a four-neck flask reactor. The obtained mixture was cooled at a temperature of 10° C. or less and methylchloroformate (MCF) 95 g (1.0 equivalent) was slowly added thereto for 2 to 3 hours while controlling temperature with strong stirring. When the adding was completed, a reaction temperature was maintained by controlling it from 10° C. up to room temperature and the reaction was complete. After the reaction was completed, the produced triethylamine (TEA) hydrochloride was filtered and removed, and the reactant was washed with a weak acid, followed by layer-separation, thereby separating an upper layer (toluene organic layer). The obtained organic layer was crystallized by concentration. After the obtained solid was filtered, the obtained cake was washed with water twice and dried. The obtained solid was a hydrazine carboxylic acid 136 g (yield 85%) having a purity of 99.1 area % by GC as a white (light yellow) solid and an intermediate, which was possible to be directly used in a next reaction without additional purification.

Example 5

Preparation of Intermediate Using Dimethylcarbonate(DMC)/NaOH

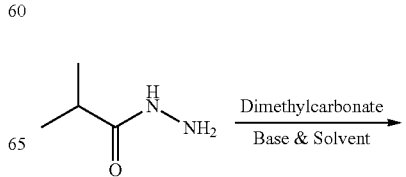

-continued

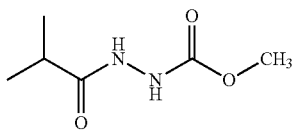

Iso-butyric acid hydrazide 102 g (1.0 mole), methanol 300 ml and NaOH (0.15 mole) (45% aqueous solution) were mixed in a four-neck flask reactor equipped with a reflux condenser, and dimethylcarbonate (DMC) 100 g (1.05 equivalent) was slowly added thereto with strong stirring. Then, a reaction temperature was maintained for 10 hours up to 60° C. and the reaction was complete. After the reaction was completed, the reactant was cooled up to room temperature. Methanol used as the reaction solvent and methanol produced as a side-product was concentrated by vacuum-evaporation to be crystallized. After the obtained solid was filtered, the obtained cake was washed with water twice and dried. The obtained solid was a hydrazine carboxylic acid 120 g (yield 74.9%) having a purity of 98.1 area % by GC as a light yellow solid and an intermediate, which was possible to be directly used in a next reaction without additional purification.

Example 6

Preparation of Intermediate Using Dimethylcarbonate(DMC)/KOH

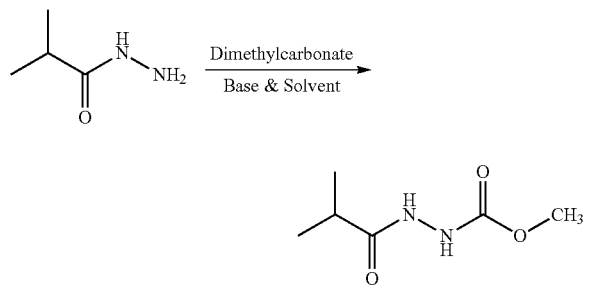

102 g (1.0 mole) of Iso-butyric acid hydrazide, 300 ml of methanol and 0.15 mole of KOH (45% aqueous solution) were mixed in a four-neck flask reactor equipped with a reflux condenser, and 100 g (1.05 equivalent) of dimethylcarbonate (DMC) was slowly added thereto with strong stirring. Then, a reaction temperature was maintained for 10 hours up to 60° C. and the reaction was completed. After the reaction was completed, the reactant was cooled up to room temperature. Methanol used as the reaction solvent and methanol produced as a side-product was concentrated by vacuum-evaporation to be crystallized. After the obtained solid was filtered, the obtained cake was washed with water twice and dried. The obtained solid was a hydrazine carboxylic acid 132 g (yield 82.5%) having a purity of 98.5 area % by GC as a light yellow solid and an intermediate, which was possible to be directly used in a next reaction without additional purification.

Example 7

Preparation of Amino-Triazolinone as Final Product Using Toluene/NaOH

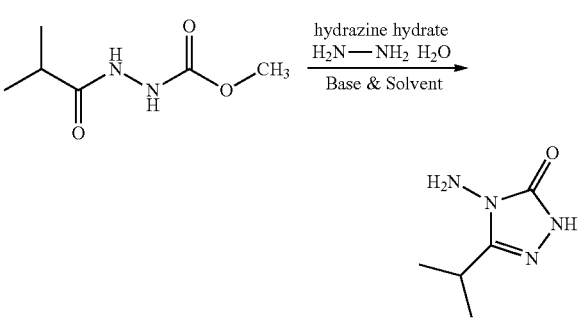

Figure 2:
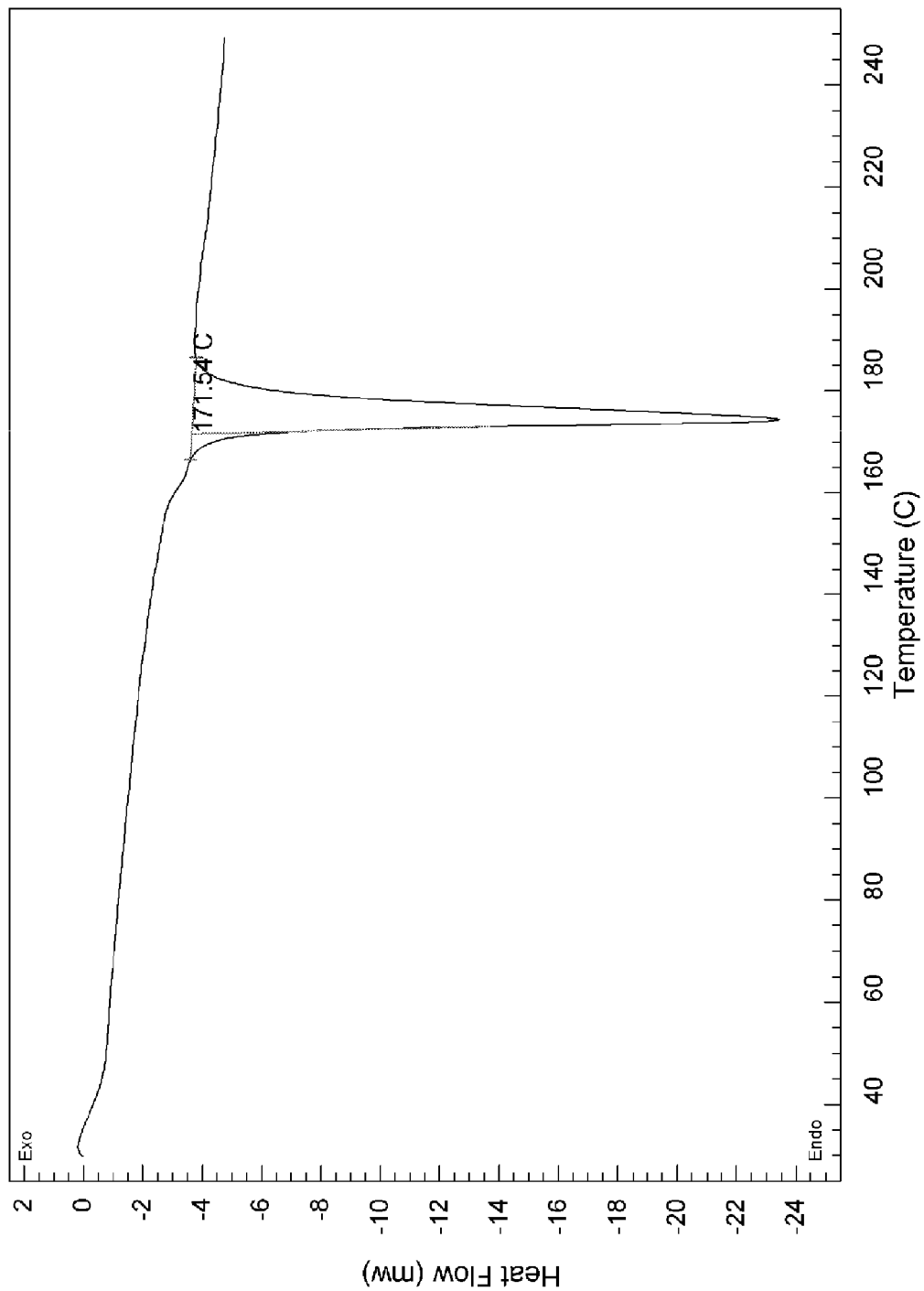
FIG. 2 shows differential scanning calorimetry (DSC) (thermal analysis) data for confirming a melting point of the final product obtained by Example 7.

160 g (1.0 mole) of the intermediate product (hydrazide-carboxylic acid) prepared by Example 1, 300 ml of toluene, 51 g (1.0 mole) of hydrazine hydride, 0.15 mole of NaOH (45% aqueous solution) were added to a four-neck flask reactor equipped with a Dean-Stark trap, and the obtained mixture was reflux-reacted at a reaction temperature of 100 to 110° C. and water produced as a side-product was removed. When it was not observed that water was removed, the reaction was completed, followed by cooling a temperature of the reactant to room temperature and water was added to the reactant, and the reactant was crystallized at 10° C. Then, after the crystallized product was neutralized (pH=7~7.5) with sulfuric acid, followed by filtration, the obtained cake was washed with water and dried to obtain a product 130 g (yield 91.4%, purity 98% (by GC), and melting point: 171.54° C.). FIG. 1 shows H-NMR data of the final product obtained by Example 7. It could be appreciated that the analysis data was the same as a data of a standard intermediate (hydrazine carboxylic acid). In addition, FIG. 2 shows differential scanning calorimetry (DSC) (thermal analysis) data for confirming a melting point of the final product obtained by Example 7. It could be appreciated from the thermal analysis data that the melting point of the obtained intermediate was 171.54° C.

Example 8

Preparation of Amino-Triazolinone as Final Product Using Toluene/KOH

The intermediate products 160 g (1.0 mole) prepared by Examples 1 to 6, 300 ml of toluene, 52.6 g (1.05 mole) of hydrazine hydride, (0.15 mole) of KOH (40% aqueous solution) were added to a Dean-Stark reactor, and the obtained mixture was reflux-reacted at a reaction temperature of 100 to 110° C. and water produced as side-product was removed. After the reaction was completed, a temperature of the reactant was cooled to room temperature, followed by adding water to the reactant, and the reactant was crystallized at 10° C. Then, after the crystallized product was neutralized (pH=7~7.5) with sulfuric acid, followed by filtration, the obtained cake was washed with water and dried to obtain 127 g of a product (yield 89.3%, purity 99.2% (by GC), MP=171 to 175° C.).

The invention claimed is:
1. A method for preparing amino-triazolinone of Chemical Formula I, the method comprising:
   (1) step of reacting an acyl hydrazide of Chemical Formula II with a carbamating agent of Chemical Formula III or IV to obtain a hydrazinecarboxylic acid of Chemical Formula V; and
   (2) step of reacting the obtained hydrazinecarboxylic acid of Chemical Formula V with a hydrazine hydrate under the presence of a base catalyst:

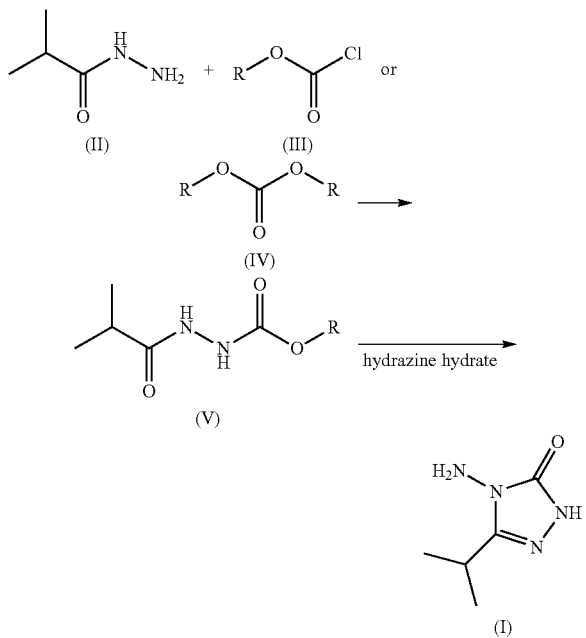

(wherein, R represents methyl, ethyl, isopropyl, or butyl).

2. The method of claim 1, wherein the carbamating agent of Chemical Formula III or IV is any one selected from a group consisting of methyl chloroformate, ethyl chloroformate, isopropyl chloroformate, dimethyl carbonate, diethyl carbonate.

3. The method of claim 1, wherein the base catalyst is any one selected form a group consisting of NaOH, KOH, $NaHCO_3$, $Na_2CO_3$, $KHCO_3$, $K_2CO_3$, and $CaCO_3$.

4. The method of claim 1, wherein the carbamating agent of Chemical Formula III used in step (1) above is methyl chloroformate (MCF), and a solvent used in step (1) above is selected from methylene chloride (MC), methanol and toluene and a reaction temperature used in step (1) above is 10 to 25° C.

5. The method of claim 4, wherein the base catalyst used in step (2) above is NaOH or KOH.

6. The method of claim 4, wherein a solvent used in step (2) above is toluene and a reaction temperature used in step (2) above is 90 to 100° C.

7. The method of claim 2, wherein the carbamating agent of Chemical Formula III used in step (1) above is methyl chloroformate (MCF), and a solvent used in step (1) above is selected from methylene chloride (MC), methanol and toluene and a reaction temperature used in step (1) above is 10 to 25° C.

8. The method of claim 7, wherein the base catalyst used in step (2) above is NaOH or KOH.

9. The method of claim 7, wherein a solvent used in step (2) above is toluene and a reaction temperature used in step (2) above is 90 to 100° C.

10. The method of claim 3, wherein the carbamating agent of Chemical Formula III used in step (1) above is methyl chloroformate (MCF), and a solvent used in step (1) above is selected from methylene chloride (MC), methanol and toluene and a reaction temperature used in step (1) above is 10 to 25° C.

11. The method of claim 10, wherein the base catalyst used in step (2) above is NaOH or KOH.

12. The method of claim 10, wherein a solvent used in step (2) above is toluene and a reaction temperature used in step (2) above is 90 to 100° C.

* * * * *